United States Patent [19]

Doersen et al.

[11] Patent Number: 5,264,358
[45] Date of Patent: Nov. 23, 1993

[54] RAT OSTEOSARCOMA CELL LINE OSR9TR1

[75] Inventors: Claus-Jens W. Doersen; Robert J. Isfort, both of Cincinnati, Ohio

[73] Assignee: The Procter & Gamble Company, Cincinnati, Ohio

[21] Appl. No.: 904,107

[22] Filed: Jun. 24, 1992

[51] Int. Cl.$^5$ .......................... C12N 5/00; C12N 5/06
[52] U.S. Cl. ................... 435/240.2; 435/240.1
[58] Field of Search ............. 435/240.2, 240.23, 70.1, 435/70.3, 69.1; 530/350, 352; 935/70, 60

[56] References Cited

U.S. PATENT DOCUMENTS 5,035,901  7/1991  Anderson et al. ................ 424/573

FOREIGN PATENT DOCUMENTS 0350641    1/1990   European Pat. Off.
2164042    3/1986   United Kingdom.
WO91/18620 12/1991  World Int. Prop. O.
WO91/18622 12/1991  World Int. Prop. O.

OTHER PUBLICATIONS

Wrana et al., Biochem. J., (1991), 273:523-531.
Rodan et al., Crit. Rev. Eukaryot. Gene Expr., (1991), 1:85-98.
"Bone-Inducing Agent (BIA) from Cultured Human Saos-2 Osteosarcoma Cells", Anderson, H. C., K. Sugamoto, D. C. Morris, H. H. T. Hsu, & T. Hunt, Bone and Mineral, 16, (1992), pp. 49-62.
"Oncogene, Tumor Suppressor Gene, and Growth Signal Transduction Alterations in a Series of Chemically-Induced Rat Osteosarcomas", Isfort, R. J., D. C. Cody, G. Lovell & C. J. Doersen, Poster Presentation, Seventh Annual Oncogene Meeting, Frederick, Md., Jun. 24, 1991.
"Growth Factors in Development, Transformation, and Tumorigenesis", Cross, M. and T. M. Dexter, Cell, vol. 64, pp. 271-280, (1991).
"Insulin Promotes Growth of the Cultured Rat Osteosarcoma Cell Line UMR-106-01: An Osteoblast-Like Cell", Hickman, J. and A. McElduff, Endocrinology, vol. 124, No. 2, pp. 701-706, (1989).
"Negative Regulators of Cell Growth", Wang, J. L. and Y. M. Hsu, TIBS 11 (1986).
"Growth Factors: Mechanism of Action and Relation to Oncogenes", Heldin, C. H. and Westermark, B., Cell, vol. 37, pp. 9-20, (1984).
"Production of An Insulin-like Growth Factor by Osteosarcoma", Blatt, J., C. White, S. Dienes, H. Friedman and T. P. Foley, Jr., Biochemical and Biophysical Research Communications, vol. 123, No. 1, pp. 373-376, (1984).

*Primary Examiner*—Margaret Moskowitz Parr
*Assistant Examiner*—Carla Myers
*Attorney, Agent, or Firm*—Braham J. Corstanje; Milton B. Graff, IV; Jerry J. Yetter

[57] ABSTRACT

The present invention relates to a novel cell line isolated from a rat osteosarcoma wherein the cell line has the following characteristics: a) a mutated p53 gene incapable of expressing p53 protein, b) a normal RB-1 gene, c) a 10-fold amplified c-myc gene, d) a normal c-fos gene, e) a deregulated immediate early gene response, f) a canalicular network MATRIGEL TM growth pattern, g) tumorigenic in congenitally athymic mice, h) no alkaline phosphatase activity, i) an ability to produce one or more growth factors selected from the group consisting of: 1) an osteoblastic differentiation growth factor, 2) a non-heparin binding mitogenic growth factor, 3) a first heparin binding mitogenic growth factor, 4) a second heparin binding mitogenic growth factor, and 5) a third heparin binding mitogenic growth factor, and j) an ability to be serially propagated greater than sixty population doublings. The present invention also relates to growth factors having the characteristics of growth factors isolated from the rat osteosarcoma cell line. The present invention also relates to a process for producing a growth factor which comprises: a) growing an osteosarcoma cell line in a culture medium, and b) recovering the growth factor from the medium. The present invention also relates to a process for producing a growth factor comprising: a) isolating mRNA from an osteosarcoma cell line which codes for the growth factor, b) making cDNA of the mRNA, c) expressing the cDNA in an expression vector, and d) recovering the growth factor.

1 Claim, 4 Drawing Sheets

RAT OSTEOSARCOMA CELL LINE OSR9TR1

TECHNICAL FIELD

This invention relates generally to a novel cell line, and specifically to a novel rat osteosarcoma cell line, as well as to certain growth factors produced by the cell line.

BACKGROUND OF THE INVENTION

Polypeptide growth factors play a key role in regulating the development of multicellular organisms and in the processes of tissue maintenance and repair. (see Cross and Dexter (1991) *Cell, Vol.* 64, pp.271-280; and Aaronson (1991) *Science,* Vol. 254, pp. 1146-1153.) At the cellular level, growth factors are involved in regulating proliferation and the progressive aquisition of the differentiated phenotype. Growth factors are capable of stimulating cellular proliferation as well as inhibiting cellular proliferation and many growth factors have been found to be multifunctional (Sporn and Roberts (1988) *Nature,* Vol. 332, pp.217-219). The highly coordinated functions of growth factors is perhaps best exemplified in the development of the hematopoiectic cell system (Metcalf (1989) *Nature,* Vol. 339, pp.27-30) where a limited number of stem cells give rise to a larger population of developmental restricted progenitor cells. These progenitors cells are further stimulated to proliferate and differentiate into the mature lymphoid, erythroid and myeloid cells. A balance between cell types and numbers of cells must be maintained throughout the developmental cascade. This requires the concerted actions of growth factors which commit a cell (now developmentally restricted) along a particular cell lineage, of growth factors which stimulate the proliferation of committed cells, and finally, of growth factors which promote the differentiation of the committed cells and inhibit the proliferation of the mature, fully differentiated cells.

Tumor cells represent naturally occurring examples of cells where the processes that control cellular proliferation and differentiation have been uncoupled (Cross and Dexter (1991) *Cell,* Vol. 64, pp.271-280; Aaronson (1991) *Science,* Vol. 254, pp.1146-1153). The observation that many types of tumor cells secrete growth factors suggests that these factors can contribute to the tumorigenic process as well as normal cellular processes. Tumor cells have been found to secrete autocrine growth factors which stimulate the proliferation of the tumor cells themselves and paracrine growth factors which stimulate surrounding cells to secret factors promoting the proliferation of the tumor cells. Paracrine factors can also stimulate the surrounding cells to provide a cellular environment promoting the survival of the tumor cells. For example, many types of tumor cells secrete growth factors that recruit endothelial cells and stimulate their proliferation and differentiation resulting in a new vasculature supplying nutrients for the tumor cells (Liotta et al., (1991) *Cell,* Vol. 64, pp.327-336).

Objects of the Present Invention

It is an object of the present invention to provide a novel rat osteosarcoma cell line.

It is also an object of the present invention to provide novel growth factors having the characteristics of a mitogenic growth factor or a differentiation growth factor.

It is also an object of the present invention to provide a process for producing novel growth factors from the novel cell line of the present invention.

SUMMARY OF THE INVENTION

The present invention relates to a novel cell line isolated from a rat osteosarcoma wherein the cell line has the following characteristics: a) a mutated p53 gene incapable of expressing p53 protein b) a normal RB-1 gene, c) a 10-fold amplified a normal c-fos gene, e) a deregulated immediate early gene response, f) a canalicular network MATRIGEL ™ growth pattern, g) tumorigenic in congenitally athymic mice, h) no alkaline phosphatase activity, i) production of an osteoblastic differentiation growth factor, j) production of a non-heparin binding mitogenic growth factor, k) production of a first heparin binding mitogenic growth factor, l) production of a second heparin binding mitogenic growth factor, and m) production of a third heparin binding mitogenic growth factor.

The present invention also relates to growth factors having the characteristics of growth factors isolated from the rat osteosarcoma cell line.

The present invention also relates to a process for producing a growth factor comprising: a) growing an osteosarcoma cell line in a culture medium, and b) recovering the growth factor from the medium.

DETAILED DESCRIPTION OF THE INVENTION

As used herein "growth factor" means a protein which has an ability to stimulate proliferation of cells or to stimulate the differentiation of cells.

As used herein "differentiation growth factor" means a protein which has an ability to stimulate the differentiation of cells.

As used herein "mitogenic growth factor" means a protein which has an ability to stimulate proliferation of cells.

As used herein, "tumorigenic" means an ability to form tumors in a host animal.

As used herein, "heparin agarose elution property of from more than X to not greater than Y M NaCl" means the molarity of NaCl used to achieve elution of a protein from heparin agarose column when a conditioned media comprising the protein is subjected to "*Fractionation of Mitogenic Growth Factors Produced by OSR9TR1*" described below, wherein X and Y is a numerical value.

As used herein, "OSR9TR1" refers to the novel cell line of the present invention, American Type Culture Collection (ATTC) No. CRL 11071.

As used herein, "OSR-2" means the cell line American Type Culture Collection (ATCC) No. CRL 11065.

As used herein, "w/v" and "v/v" means percent by weight and percent by volume, respectively.

The present invention relates to a novel cell line isolated from a rat osteosarcoma wherein the cell line has the following characteristics: a) a mutated p53 gene incapable of expressing p53 protein b) a normal RB-1 gene, c) a 10-fold amplified c-myc gene, d) a normal c-fos gene, e) a deregulated immediate early gene response, f) a canalicular network MATRIGEL ™ growth pattern, g) tumorigenic in congenitally athymic mice, h) no alkaline phosphatase activity, i) an ability to produce one or more growth factors selected from the group consisting of: 1) an osteoblastic differentiation growth factor, 2) a non-heparin binding mitogenic growth factor, 3) a first heparin binding mitogenic growth factor, 4) a second heparin binding mitogenic growth factor, and 5) a third heparin binding mitogenic growth factor, and j) an ability to be serially propagated greater than sixty population doublings; wherein the osteoblastic differentiation growth factor has the following characteristics: i) an ability to stimulate the differentiation of multipotent cells to osteoblastic cells; the non-heparin binding mitogenic growth factor has the following characteristics: i) an inability to bind to heparin agarose gel, ii) an ability to stimulate the proliferation of osteoblastic cells, and iii) an ability to stimulate the proliferation of fibroblast cells; the first heparin binding mitogenic growth factor has the following characteristics: i) a heparin agarose elution property of from greater than 0 to less than or equal to 0.2 M NaCl, and ii) an ability to stimulate the proliferation of fibroblast cells; the second heparin binding mitogenic growth factor has the following characteristics: i) a heparin agarose elution property of from greater than 0.2 to less than or equal to 1.0M NaCl, and ii) an ability to stimulate the proliferation of fibroblast cells; and the third heparin binding mitogenic growth factor has the following characteristics: i) a heparin agarose elution property of from greater than 1.0 to about 2.0 M NaCl, and ii) an ability to stimulate the proliferation of osteoblstic cells. Preferably, the cell line has the characteristics of American Type Culture Collection Accession No. CRL 11071.

The present invention also relates to growth factors having the characteristics of the above identified growth factors.

The present invention also relates to a process for producing a growth factor comprising: a) isolating mRNA from an osteosarcoma cell line which codes for the growth factor, b) making cDNA of the mRNA, c) expressing the cDNA in an expression vector, and d) recovering the growth factor.

An alternative way of obtaining the growth factors produced by the cell line of the present invention is by isolation of the growth factor mRNA for use by those skilled in the art for expression of the protein of interest. Protein expression from mRNA covers a wide variety of techniques including PCR methodologies using a number of organisms for the final expression of the protein including bacteria, fungus, animal cells, insect cells and pl ant cells as well as noncellular protein expression methodologies (for an overall review of molecular biology techniques used in protein expression cloning see Sambrook et al. (1989) *Molecular Cloning—A Laboratory Manual,* 2nd edition, Cold Spring Harbor Laboratory Press, Cold Spring Harbor, N.Y.). Briefly, this procedure involves isolating mRNA from a osteosarcoma cell line which codes for the growth factor, making cDNA of the mRNA expressing the cDNA in an expression vector, and recovering a recombinant form of the growth factor. Preferably, this procedure involves isolating mRNA from an osteosarcoma cell line which codes for the growth factor, making cDNA of the mRNA, cloning the cDNA into an expression vector, expressing the cDNA in a host, and recovering a recombinant form of the growth factor. More preferably, this procedure involves isolation of mRNA from the osteosarcoma cell, making cDNA from the mRNA, cloning of the cDNA into an appropriate expression source, expression of the protein of interest from the cDNA inserted into the expression vector, screening the expression source for the protein of interest, purifying the expression clone containing the cDNA coding for the protein of interest, and expression of this purified cDNA in an expression vector in an appropriate expression source for large scale synthesis of the protein of interest. Multiple technical variations of this general expression schemes are well understood by those skilled in the art and all would apply.

The cell line of the present invention is useful as a biological source for the growth factors of the present invention and/or the mRNA coding for such growth factors. The growth factors of the present invention are useful for one or more of the following: 1) treating diseases affecting the bone and cartilage (e.g., those growth factors demonstrating an ability to stimulate osteoblast cells), and 2) wound healing (e.g., those growth factors demonstrating an ability to stimulate fibroblast cells and osteoblast cells).

Statement of Deposit

OSR9TR1 has been deposited at The American Type Culture Collection, 12301 Parklawn Drive, Rockville, Md. 20852, U.S.A., on Jun. 5, 1992. The deposited strain has been assigned Accession No. CRL 11071.

The subject cultures have been deposited under conditions that assure access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that Applicant granting of permission to the depository to distribute samples of the deposit does not constitute an express or implied license to practice the invention claimed in any patent issuing on the subject application or any other patent.

The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Establishment of the OSR9TR1 Cell Line

A cell line was established from a tumor excised from a Sprague-Dawley rat with osteosarcoma. The site of the excised tissue was the right tibia. The tumor tissue was aseptically remove from the euthanized animal and carefully trimmed of connective tissues. The tumor was minced in a culture dish (100 mm diameter) containing 15 ml of growth medium (10% fetal bovine serum, 90% RPMI 1640 medium (GIBCO)) further supplemented with penicillin (100 units/ml, GIBCO), Fungizone (0.25 microgram/ml, GIBCO) and streptomycin (100 micrograms/ml,GIBCO), and incubated at 37° C. in an atmosphere of 5% $CO_2$ and 95% air with a relative humidity of approximately 95%. The adherent cells which migrated from the minced tumor pieces onto the surface of the culture dish were further expanded as a cell population using standard tissue culture techniques. Once the rat osteosarcoma cell line reached confluence in a tissue culture flask (150 cm$^2$ surface area), the cell line was designated as having a mean population doubling of 1. At this stage, the cells were subcultured in growth medium (10% fetal bovine serum, 90% RPMI 1640 medium) with no antibiotic or antimycotic supplements. The rat osteosarcoma cell line was routinely tested for mycoplasma contamination by DAPI assay (Stanbridge (1981) Isr. J. Med. Sci., Vol. 17, pp.563-568) and was found to be negative.

The rat osteosarcoma cell line was found to be highly tumorigenic when assayed for tumor formation in congenitally athymic mice (a nude mouse, product of Harlan Sprague Dawley, Inc.). The rat osteosarcoma cells at a mean population doubling of 9, were injected subcutaneously in the mid-flank region of the animals at an innoculum of approximately $1 \times 10^7$ cells per site. A total of eight sites (two per animal) were injected, and tumors arose at 100% of the sites. One of these tumors was aseptically excised from the euthanized animal and the tumor cell population was re-established in culture according to the methods described above for the establishment of the original tumor cell population. Once the cells reached confluency in a 150 cm$^2$ tissue culture flask, the cells were designated as OSR9TR1 at a mean population doubling of 1. These cells were found to be free of mycoplasma contamination by the DAPI assay (Stanbridge (1981) Isr. J. Med Sci., Vol. 17, pp. 563-568).

Characteristics of the OSR9TR1 Cell Line

The OSR9TR1 cell line can be serially propagated in culture, with no known limited life span. The OSR9TR1 cell line displays a limited, immature osteoblast-like phenotype in vitro. The cells show no staining for the presence of alkaline phosphatase (Rodan and Rodan (1983) Bone and Mineral Research, Annual 2 (Peck, ed.) pp. 244-285) as detected by a cytochemical assay (Sigma Chemical Company, Procedure 85). It has been reported (Vukicevic et al., (1990) Cell, Vol. 63, pp. 437-445) that osteoblastic cells are capable of forming cell clusters exhibiting networks of canalicular cell processes when cultured on reconstituted basement membrane extracts such as MATRIGEL TM (solubilized tissue basement membrane available from Collaborative Biomedical Products Bedford, Mass., containing laminin, collagen type IV, heparin sulfate proteoglycan and entactin). Fibroblasts, chondrocytes and embryonic stem cells did not demonstrate the canalicular cell processes. OSR9TR1 cells when cultured on MATRIGEL TM at a density of approximately 50,000 cells per well of a standard 24-well tissue culture plate demonstrated a large mass of cells with a network of canalicular cell processes. This growth pattern was distinct from smaller cell clusters with the characteristic canalicular processes that are formed by the osteoblastic MC3T3-E1 cells plated at an equivalent density (Sudo et al., (1983) J. Cell Biol., Vol. 96, pp. 191-198; Vukicevic et al., (1990) Cell, Vol. 63, pp. 437-445). The differences in the size of the cell masses displaying the canalicular processes may be due to the tumorigenic properties of the OSR9TR1 cells.

Molecular Characterization of the OSR9TR1 Cell Line

In order to characterize the OSR9TR1 cell line in terms of unique mutations which can identify this cell line we have screened the cell line for mutations in genes which are commonly mutated in osteosarcomas. This molecular fingerprint of the OSR-9TR1 cell provides a convenient and useful way to identify this cell line because these mutations are critical for the growth of these cells and is not expected to change.

In this respect human osteosarcomas have been extensively studied with respect to mutations in the retinoblastoma (RB-1) and p53 tumor suppressor genes (Iavarone et al., (1992) Proc. Natl. Acad. Sci. USA, ZVol. 89, pp. 4207-4209; Diller et al., (1990) Mol. Cell. Biol., Vol. 10, pp. 5772-5781; Masuda et al., (1987) Proc. Natl. Acad. Sci. USA, Vol. 84, pp. 7716-7719; Levine and Momand (1990) Biochem. et Byophys. Acta, Vol. 1032, pp. 119-136; Miller et al., (1990) Cancer Res., Vol. 50, pp. 7950-7954; Friend et al., (1987) Proc. Natl. Acad. Sci. USA, Vol. 84, pp. 9059-9063; Mulligan et al., (1990) Proc. Natl. Acad. Sci. USA, Vol. 87, pp. 5863-5867; Hansen et al., (1985) Proc. Natl. Acad. Sci. USA, Vol. 82, pp. 6216-6220; Horowitz et al., (1989) Science, Vol. 243, pp. 937-940; Toguchida et al., (1989) Nature, Vol. 338, pp. 156-158). RB-1 mutations include point mutations, deletions, and splicing mutations (Friend et al., (1987) Proc. Natl. Acad. Sci. USA, Vol. 84, pp. 9059-9063; Levine and Momand, (1990) Biochem. et Biophus. Acta, Vol. 1032, pp. 119-136; Mori et al., (1990) Oncogene, Vol. 5, pp. 1713-1717; Horowitz et al., (1989) Science, Vol. 243, pp. 937-940). All of these mutations result in the production of a non-functional RB-1 protein. RB-1 is believed to function by acting as a "brake" on cellular proliferation at the appropriate time in the cell cycle Control of the RB-1 function is achieved by selective and timely phosphorylation of RB-1 protein; phosphorylated RB-1 allows cellular proliferation while unphosphorylated RB-1 protein inhibits cellular proliferation (Laiho et al., (1990) Cell, Vol. 62, pp. 175-185; DeCaprio et al., (1989) Cell, Vol. 58, pp. 1085-1095; Buchkovich et al., (1989) Cell, Vol. 58, pp. 1097-1105; Chen et al., (1989) Cell, Vol. 58, pp. 1193-1198; Furukawa et al., (1990) Proc. Natl. Acad. Sci. USA, Vol. 87, pp. 2770-2774). RB-1 control of cellular proliferation is one part of a closely regulated network of cell cycle controls, which include the cell cycle control proteins c-myc, c-fos and TGF-B (Laiho et al., (1990) Cell, Vol. 62, pp. 175-185; Moses et al., (1990) Cell, Vol. 63, pp. 245-247; Robbins et al., (1990) Nature, Vol. 346, pp. 668-671).

The p53 tumor suppressor gene was originally identified as an SV40 large T antigen binding protein whose expression was greatly increased (approximately 5-100 fold at the protein level) during SV40 cellular transformation (Levine and Momand, (1990) Biochem. et Biophus. Acta, Vol. 1032, pp. 119-136; Levi ne et al., (1991) Nature, Vol. 351, pp. 453-456). The p53 gene has since been found to be mutated in a variety of tumor types (Hollstein et al., (1991) Science, Vol. 253, pp. 49-53)

including human osteosarcoma cells (Mulligan et al., (1990) *Proc. Natl. Acad. Sci. USA*, Vol. 87, pp. 5863-5867; Miller et al., (1990) *Cancer Res.*, Vol. 50, pp. 7950-7954; Masuda et al., (1987) *Proc. Natl. Acad. Sci. USA*, Vol. 84, pp. 7716-7719; Diller et al., (1990) *Mol. Cell. Bio.*, Vol. 10, pp. 5772-5781). Mutation of the p53 gene either results in an altered protein which does not function normally or a complete loss of protein. Both of these mechanisms result in the absence of a functional p53 protein (Halevy et al., (1990) *Science*, Vol. 250, pp. 113-116; Chen et al., (1990) *Science*, Vol. 250, pp. 1576-1580; Milner and Medcalf, (1991) *Cell*, Vol. 65, pp. 765-774) and cellular transformation. The p53 protein is believed to function in several ways. The p53 protein is a transcriptional activator since p53 protein binds to specific DNA sequences (Raycroft et al., (1990) *Science*, Vol. 249, pp. 1049-1051; Kern et al., (1991) *Science*, Vol. 252, pp. 1708-1711) and contains an $NH_2$-terminal acidic domain which efficiently activates the transcription of genes in both yeast and mammalian cells (Fields and Jang, (1990) *Science*, Vol. 249, pp. 1046-1049). The protein produced from mutated p53 genes does not transcriptionally activate responsive genes (Raycroft et al., (1990) *Science*, Vol. 249, pp. 1049-1051). In addition, p53 regulates DNA replication since wild-type protein but not protein from mutated p53 genes associates with replication complexes (Levine et al., (1991) *Nature*, Vol. 351, pp. 453-456; Levine and Momand, (1990) *Biochem. et Biophus. Acta*, Vol. 1032, pp. 119-136) and is phosphorylated by p34(cdc2)-p60 and p34(cdc2)-cyclin B complexes (Bischoff et al., (1990) *Proc. Natl. Acad. Sci. USA*, Vol. 87, pp. 4766-4770; Milner et al., (1990) *EMBO J*, Vol. 9, pp. 2885-2889).

Two additional transforming genes which have been implicated in human and non-human osteosarcoma formation are the fos and myc oncogenes. The oncogenic variant of c-fos, v-fos, was first isolated as the transforming gene in retroviruses which resulted in murine osteosarcoma formation (Varmus (1984) *Ann. Rev. Genet.*, Vol. 18, pp. 553-612). Interestingly, transgenic mice carrying the v-fos oncogene display both cartilage and osteosarcoma tumors (Wang et al., (1991) *EMBO J*, Vol. 10, pp. 2437-2450). Oncogenic mutation of c-fos results when the fos gene is either overexpressed or inappropriately expressed as a result of either viral transduction or mutation. C-fos functions in the cell, in conjunction with c-jun as the complex which binds the AP-1 transcriptional activation site (Abate et al., (1990) *Science*, Vol. 249, pp. 1157-1161; Sassone-Corsi et al., (1988) *Cold Spring Harbor Symposia on Quantative Biology LIII*, pp. 749-760).

C-myc has been found to be mutated both in radiation induced murine osteosarcomas (Sturm et al., (1990) *Cancer Res.*, Vol. 50, pp. 4146-4153) and in primary human osteosarcoma tumors (Bogenmann et al., (1987) *Cancer Res.*, Vol. 47, pp. 3808-3814). The myc oncogene was originally identified as the transforming gene in several retroviruses (v-myc) and c-myc mutations in a variety of tumor types were later identified (DePinho et al., (1987) *J. Cell Biochem.*, Vol. 33, pp. 257-266; Varmus (1984) *Ann. Rev. Genet*, Vol. 18, pp. 553-612). C-myc is most commonly amplified or translocated, both of which, along with retroviral transduction, result in the inappropriate expression of the myc gene (Varmus (1984) *Ann. Rev. Genet.*, Vol. 18, pp. 553-612; DePinho et al., (1987) *J. Cell Biochem*, Vol. 33, pp. 257-266). Myc protein and the Max protein form a complex which binds the regulatory region of genes, via a unique sequence, to control their expression (Blackwood and Eisenman, (1991) *Science*, Vol. 251, pp. 1211-1217; Cole (1991) *Cell*, Vol. 65, pp. 715-716). C-myc, along with c-fos are immediate early genes and are believed to play a central role in mitogenic signalling in the cell (Rozengurt (1986) *Science*, Vol. 234, pp. 161-166).

An additional way to assay c-fos and c-myc functional activity is to determine if theses genes are transcriptionally activated following mitogenic stimulation. C-fos and c-myc are both members of a class of genes called the immediate early genes(Sassone-Corsi et al., (1988) *Cold Spring Harbor Symposia on Quantitative Biology LIII*, pp. 749-760; Depinho et al., (1987) *J. Cell. Biochem*, Vol. 33, pp. 257-266). Genes in this class are transcriptionally activated following mitogenic stimuli usually within 1 hour and without the need of protein synthesis (Almendral et al., (1988) *Mol. Cell. Biol.*, Vol. 8, pp. 2140-2148; Greenberg et al., (1986) *Mol. Cell. Biol.*, Vol. 6, pp. 1050-1057). Since this is a complex pathway, alterations in immediate early gene transcription is indicative of either a mutation in the cellular pathway which leads from the receptor/plasma membrane to the gene/nucleus of the cell or a mutation which leads to the autocrine expression of a growth factor. Either of the above mutated phenotypes lead to a downregulation and subsequent inhibition of expression of the c-myc and c-fos genes following serum starvation and mitogen stimulation.

Characterization of Tumor Suppressor Genes and Oncogenes

High molecular weight DNA was isolated from the OSR9TR1 cell line as follows. Approximately $1 \times 10^8$ cells were cultured as described above until confluent. These cells were then scraped off the tissue culture flask into culture media, collected by centrifugation at 3300 g for 5 minutes, the culture media was removed from the cell pellet and the pellet was resuspended in 9.5 ml of NET buffer (100 mM sodium chloride, 10 mM Tris—pH 8.0, 1 mM EDTA). To the resuspended DNA was added 50 ul of 10 mg/ml of proteinase K (Boehringer Mannheim) and 0.5 ml of 10% (w/v) sodium dodecyl sulphate/water. This mixture was mixed well and incubated at 55° C. for one hour followed by extraction twice with an equal volume of a 50:50 mixture of phenol:chloroform. The aqueous phase was collected by centrifugation at 3300 g for 5 minutes and reextracted with an equal volume of chloroform. The aqueous phase was collected by centrifugation at 3300 g for 5 minutes, removed to a new tube and to i t was added 1 ml of 3M sodium acetate pH 5.2 and 20 ml of 100% ethanol. This solution was mixed well and incubated at −20° C. for 2 hours followed by the collection of high molecular weight DNA by centrifugation at 3300 g for 30 minutes. The high molecular weight DNA was washed once with 5 ml of 70v/v.% (ethanol/water), dried and resuspended in TE (10 mM Tris-pH 8.0 and 1 mM EDTA) at a concentration of I mg/ml.

For restriction enzyme analysis, 20 ug of the above isolated high molecular weight DNA in 20 ul TE was added to 2.5 ul of 10× restriction enzyme buffer (1× restriction enzyme buffer consist of 50 mM Tris—pH 8.0, 10 mM magnesium chloride, and 100 MM sodium chloride) and 2 ul of restriction enzyme (either Eco R1 or Hind III at 10 units/ml both from New England Biolabs) and this mixture was incubated at 37° C. for 16 hours. Following incubation, the above solution was added to 3 ul of 10× gel loading buffer (10× gel loading buffer is 0.25% bromophenol blue, 0.25% xylene cyanol, 25% Ficoll type 400, 10 MM EDTA in water) and the restriction endonuclease generated fragments were separated by agarose gel electrophoresis. Agarose gel electrophoresis was performed as follows. A 0.6% (W/v) agarose (Bethesda Research Laboratories) gel in 1× TBE (1× TBE consist of 0.089 M Tris, 0.089 M boric acid, and 0.002 M EDTA) was poured in a BioRad horizontal gel electrophoresis apparatus, the above DNA solution was loaded into a well and electrophoresis was performed in a 1× TBE solution for 16 hours at 20 volts. Following electrophoresis, the gel was stained for 1 hour in 0.5 ug/ml ethidium bromide (Sigma Chemical Company)/water solution followed by photography under 302 nm ultraviolet light irradiation. The gel was then prepared for Southern blotting as follows. The gel was soaked for 1 hour in a solution of 1.5M sodium chloride and 0.5M sodium hydroxide with constant shaking followed by an incubation for 1 hour in a solution of 1.5M sodium chloride and 1M Tris—pH 8.0 with constant shaking. The gel was then transferred to an LKB VacuBlot apparatus (LKB Scientific) prefitted with a sheet of BAS-NC nitrocellulose (Schleiser and Schuel) and the transfer of DNA from the agarose gel to the nitrocellulose membrane was performed under 40 cm.H$_2$O of pressure using 10×SSC (10× SSC is 1.5M sodium chloride and 0.15M sodium citrate, pH 7.0) as the transfer medium. The OSR-2 (ATCC No. 11065) DNA Southern blot was then used in a hybridization analysis as follows. The nitrocellulose filter was first wet in 6× SSC followed by prehybridization in hybridization buffer [50% formamide (molecular biology grade, Bethesda Research Laboratories), 5× Denhardt's solution (Denhardt's solution is 0.1% Ficoll, 0.1% polyvinylpyrrolidone, and 0.1% bovine serum albumin—pentax fraction V—all from Sigma Chemical Company), 5× SSPE (20× SSPE is 3M sodium chloride, 0.2M sodium phosphate, and 0.02M EDTA—pH 7.4), 0.1% sodium dodecyl sulphate, and 100 ug/ml of denatured salmon sperm DNA (Sigma Chemical Company)] for 4 hours at 42° C. with constant agitation. Molecular probes for the tumor suppressor genes RB-1 (ATCC #57450) and p53 (Levine and Momand (1990) *Biochemics et Biophysics Acta,* Vol. 1032, pp119–136) and the oncogenes c-myc (ATCC #41008) and c-fos (ATCC #41040) were radiolabelled using an Amersham nick translation kit and [$^{32}$p]dCTP (ICN) to a specific activity of $1\times10(8)$ cpm/ug DNA by following the manufacturers recommendations. These radiolabelled probes were then added to the hybridization solution/nitrocellulose filter of the prehybridization step and incubated at 42° C. for 40 hours with constant agitation. Following hybridization, the nitrocellulose filters (blots) were first incubated in 2× SSC and 0.1% SOS at room temperature for 1 hour followed by an incubation in 0.2× SSC and 0.1% SDS at 65° C. for 1 hour. The results of the hybridization experiment were visualized by autoradiography at −70° C. Following autoradiography, the films were developed and used in data analysis.

The molecular analysis of the OSR9TR1 cell line RB-1, p53, c-myc and c-fos genes indicated that the RB-1, p53 and c-fos genes appeared normal (non-mutated, wild-type) as compared to a non-tumorigenic Sprague-Dawley rat cell control at the above described level of analysis (restriction enzyme analysis and Southern blotting). The c-myc gene was amplified 10 fold as compared to a non-tumorigenic Sprague-Dawley rat cell control.

RB-1 and p53 Protein Analysis

Immunological identification of the p53 and RB-1 proteins were performed as follows. $1\times10^6$ OSR9TR1 cells were labelled for 4 hours with 100 uCi/ml of [$^{35}$S]methionine (TranSlabel—ICN) in methionine-free RPMI-1640 (GIBCO) media containing 10% fetal bovine serum for 4 hours at 37° C. Following labelling, the cells were scraped off the tissue culture plastic into the labelling media, the cells were collected by centrifugation at 3300 g for 5 minutes, followed by removal of the labelling media and the snap freezing of the cell pellet in liquid nitrogen. The frozen cell pellets were dissolved in 1 ml of ice-cold lysis buffer (50 MM Tris—pH 8.0, 5 mM EDTA, 150 mM sodium chloride, 0.5% Nonidet P-40, and 1 mM phenylmethylsulfonylfluoride) by vigorous vortexing and incubated on ice with intermediate vortexing for 30 minutes. The lysates were clarified of nonsoluable material by centrifugation at 10,000 g for 30 minutes, the supernate was removed to a new tube to which was added 10 ul of antibodies specific for either mutant p53 (Oncogene *Science*p53 Ab-3), normal and mutant p53 (Oncogene *Science*p53 Ab-1), or RB-1 (a 50:50 mixture of Oncogene *Science*RB Ab-2 and Ab-3), and 50 ul of a Protein A/G agarose (Boehringer Mannheim):lysis buffer (50:50). The above mixture was incubated overnight at 4° C. with constant shaking. The cell lysate was aspirated off and the antigen/antibody/protein A-G pellet was washed one time in 1 ml of lysis buffer, one time in 1 ml of SNTE buffer (50 MM Tris-pH 7.4, 5 mM EDTA, 5% sucrose - w/v, 1% Nonidet P-40, and 0.5 M sodium chloride), and one time in 1 ml of RIPA buffer (50 MM Tris —pH 7.4, 150 mM sodium chloride, 1% Triton X-100, 0.1% sodium dodecyl sulphate and 1% sodium deoxycholate). Following washing, the antigen/antibody/protein A-G agarose pellet was redissolved in 25 ul of sample buffer (62.5 mM Tris—pH 6.8, 2% sodium dodecyl sulphate, 10% glycerol, 5% 2-mercaptoethanol), boiled at 100° C. for 2–3 minutes, and applied to a well of a 10% SDS-PAGE gel. SDS-PAGE was performed as described by Laemmli (Laemmli, U.K. (1970) *Nature*, Vol. 227, pp. 680–685) for 6–8 hours at 30 mA constant current per gel. Following electrophoresis, the SDS-PAGE gels were incubated in 30% methanol and 10 % acetic acid for at least 1 hours, impregnated with EN3NANCE (NEN-DuPont) according to the manufacturers recommendations, dried onto Whatman 3 mm paper using a BioRad gel dryer set at 60° C. for 2 hours and autoradiography at −70° C. was performed.

The results of the p53 and RB-1 protein analysis of the OSR9TR1 cell line indicated that the OSR9TR1 p53 protein was deleted because we failed to detect p53 protein with either of the above described p53 antibodies. These results indicate that while the gene suffered no major alteration (deletion, duplication, etc) it had suffered a point mutation or a minor deletion which resulted in the loss of protein expression. The deletion of p53 protein in transformed cells has been observed previously (Levine et al., (1991) *Nature*, Vol. 351, pp. 453–456; Hollstein et al., (1991) *Science*, Vol. 253, pp. 49–53; Gannon et al., (1990) *EMBO J.*, Vol. 9, pp. 1595–1602; Diller et al., (1990) *Mol. Cell. Biol.*, Vol. 10, pp. 5772–5781). The RB-1 protein was normal both in its level of expression and its physical characteristics, indicative of a wild-type gene.

Immediate Early Gene Expression Following Mitogen Stimulation

In order to characterize the immediate early gene (c-myc and c-fos) transcription following mitogen stimulation in the OSR9TR1 cell line the following experiments were performed. Approximately $1 \times 10^8$ cells were grown to 70% confluence in a tissue culture flask in 25 ml of standard growth media. The cells were washed 2 time with serum-free media followed by the addition of 25 ml of serum-free culture media and incubated for 12-16 hours at 37° C. under an atmosphere of 10% carbon dioxide in an incubator. To the serum-starved cells was added 3 ml (10% v/v) of fetal bovine serum and 10 ug/ml of cycloheximide and the cells were incubated as above for 3 hours. One group of cells was not mitogen stimulated and remained serum-starved. RNA from the mitogen stimulated and non-stimulated cells was isolated using the RNAzol (Cinna/Biotecx Inc.) methodology according to the manufacturer's recommendation. Briefly, $1 \times 10^8$ cells were lysed in situ with 10 ml of RNAzol, the lysate was collected, I ml of chloroform was added to the lysate, the samples were vortexed vigorously for 15 seconds, and the mixture was then centrifuged at 12,000 g (40° C.) for 15 minutes. The upper (aqueous) phase was transferred to a new tube, an equal volume of isopropanol was added to it, the samples were cooled to $-20°$ C. for 45 minutes, followed by pelleting of the RNA by centrifugation at 12,000 g (40° C.) for 15 minutes. The pelleted RNA was washed once with ice-cold 70% ethanol/water, dried, and resuspended in RNAse-free water at 20 ug/4.5 ul. RNA formaldehyde agarose gel electrophoresis was performed as described (Sambrook et al., (1989) Molecular Cloning, Cold Spring Harbor Press, Cold Spring Harbor, N.Y.). Briefly, 20 ug of total cellular RNA was denatured by heating to 55° C. for 15 minutes in denaturation buffer [4.5 ul RNA solution, 2.0 ul $10 \times$ RNA gel buffer (0.2M MOPS—pH 7.0, 50 MM sodium acetate, and 10 mM EDTA), 3.5 ul formaldehyde and 10.0 ul formamide] followed by the addition of 2 ul of loading buffer (50% glycerol, 1 mM EDTA, 0.4% bromophenol blue, and 0.4% xylene cyanol) and loading of the sample into a well of the formaldehyde gel (1% agarose, 20 mM MOPS—pH 7.0, 5 mM sodium acetate, I MM EDTA and 2.2 M formaldehyde). Electrophoresis was performed at 30 volts (constant voltage) for 16 hours. Following electrophoresis the gel was stained with ethidium bromide (0.5 ug/ml in water) for 1 hour, destained in water for 1 hour, and photographed under 300 nm ultraviolet light using a Foto/Prep I (Fotodyne) transilluminator. Following photography, the gel was transferred to nitrocellulose (Schleicher & Schuell, BA-S NC) using a LKB Vacugene vacublotting apparatus operating at 50 cm.$H_2O$ with a $20 \times$ SSC (3 M sodium chloride and 0.3 M sodium citrate—pH 7.0) fluid transfer medium. Following transfer, the RNA was fixed to the nitrocellulose filter by UV irradiation using a Stratalinker (Stratagene Inc.) UV crosslinker at 0.12 Joules/$CM^2$. Following RNA fixation, the Northern blots were used in probe hybridization studies following previously described procedures (Sambrook et al., (1989) Molecular Cloning, Cold Spring Harbor Press, Cold Spring Harbor, N.Y.) that were modified as follows. The probes of interest, c-fos (ATCC #41040) or c-myc (ATCC #41008) were radio-actively labelled by using an Amersham nick translation kit following the manufacturer's recommendations. Briefly, 1 ug of probe DNA was incubated with $1 \times$ nick translation buffer, 50 uCi alpha [$^{32}$p]-dCTP (NEN), and polymerase mix in a total volume of 20 ul at 15° C. for 2 hours followed by the addition of 80 ul of 1X STE (100 mM sodium chloride, 10 mM Tris—pH 8.0, and 1 MM EDTA). Separation of the incorporated from non-incorporated nucleotides was achieved using a Biospin column (BioRad). Typically 1 ug of probe had a specific activity of greater than $1 \times 10^8$ dpm. Following nick translation, the probe was boiled for 10 minutes and added to a prehybridized filter (4 hours in hybridization solution at 42° C.) in 10 ml of hybridization solution [$6 \times$ SSPE (3M sodium chloride, 0.2 M sodium phosphate—pH 7.4 and 20 MM EDTA), $5 \times$ Denhardt's solution (1% Ficoll, 1% polyvinyl- pyrrolidone, and 1% BSA—Pentax fraction V), 0.5% sodium dodecyl sulfate, 100 ug/ml denatured—sonicated salmon sperm DNA, and 50% formamide] and incubated for 48 hours at 42° C. Following hybridization the filters were washed at room temperature in $2 \times$ SSC—0.1% SDS followed by a wash at 65° C. with $0.2 \times$ SSC—0.1% SDS. The filters were then dried, mounted to 3MM paper (Whatman) and autoradiography at $-80°$ C. was performed using intensifying screens (NEN).

The OSR9TR1 cell line displayed an altered immediate early gene response with a constitutive expression of c-myc, even in the absence of added growth factor, and an absence of transcriptional upregulation of the c-fos gene in response to mitogen stimulation.

TABLE 1

| Characterizations of the OSR-9TR1 cell line |
| --- |
| The OSR9TR1 cell line has the following characteristics;<br>a. a mutated p53 gene incapable of expressing p53 protein<br>b. a normal RB-1 gene,<br>c. a 10-fold amplified c-myc gene,<br>d. a normal c-fos gene,<br>e. a deregulated immediate early gene response,<br>f. a canalicular network MATRIGEL ™ growth pattern,<br>g. tumorigenic in congenitally athymic mice,<br>h. no alkaline phosphatase activity,<br>i. an ability to produce one or more growth factors selected from the group consisting of:<br>  1) an osteoblastic differentiation growth factor,<br>  2) a non-heparin binding mitogenic growth factor,<br>  3) a first heparin binding mitogenic growth factor,<br>  4) a second heparin binding mitogenic growth factor, and<br>  5) a third heparin binding mitogenic growth factor; and<br>j. an ability to be serially propagated greater than sixty population doublings. |

Use of the OSR9TR1 Cell Line as a Source of Growth Factors

The ability of a growth factor to stimulate DNA synthesis in a serum-starved quiescent cell is perhaps the most widely studied response to growth factors. This ability to stimulate the proliferation or differentiation of a target cell is an indicator of the growth factor's ability to stimulate proliferation or to stimulate differentiation of cells. The mitogenic response of cells can be quantitated using a [$^3$H]thymidine incorporation assay as previously described (Isfort (1990) Somatic Cell Molec. Genet., Vol. 16, pp. 109-121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. Mitogens such as serum and various growth factors are added to the serum starved cells in a volume of 50 ul of medium, with serum-free medium serving as a control. After 16 hours incubation, the cells are exposed to 1 μCi of [$^3$H]thymidine for 6 additional hours of incubation. The cells are then harvested and lysed on glass fiber filters using a PHD cell harvester (Cambridge Technology, Inc.) and the radioactivity in the samples was assayed by scintillation spectrophotometry.

To test for the secretion of mitogenic growth factors by OSR9TR1 cells, serum-free conditioned medium was harvested from cell cultures. OSR9TR1 cells were grown to confluency in a 150 cm$^2$ tissue culture flask. The growth medium was removed and the cell monolayer was rinsed three times with approximately 15 ml of phosphate buffered saline. The cells were then incubated in 25 ml of serum free medium for approximately 24 hours, and the conditioned medium was harvested and clarified by centrifugation for 15 minutes at 2000 xg. The conditioned medium was stored at −20° C. until assayed. The aseptic quality of the conditioned medium was assured by sterile centrifugal filtration (Centrex filters, Schleicher and Schuell).

A panel of target cells was used which incorporated osteoblastic, fibroblastic and multipotential mesenchymal cell types. These include the osteoblastic cells OSR-2 (ATCC No. CRL 11065) and MC3T3-El (Sudo et al., (1983) J. Cell Biol., Vol. 96, pp. 191-198); the fibroblastic cell line MRC-5 (American Type Culture Collection, CCL 171); the multipotential cell line, C3H10T½, clone 8 (American Type Culture Collection, CCL 226); and the multipotential cell population isolated from neonatal rat muscle (designated NRM) according to slight modifications of the procedure describe by Sampath et al., (1984) Proc. Natl. Acad. Sci. USA, Vol. 81, pp. 3419-3423. Briefly, the tricep muscles were aseptically isolated from euthanized newborn Sprague-Dawley rats and cleaned of connective and vascular tissue. The muscles were minced and cultured in 15 ml of 10% fetal bovine serum, 90% CMRL-1066 medium (GIBCO) supplemented with antibiotics and antimycotic mixture (penicillin, 100 units/ml; streptomycin, 100 ug/ml; Fungizone, 0.25 ug/ml, GIBCO). Once the explant cultures reached confluence in a 150 cm$^2$ tissue culture flask, the NRM cell line was designated as being at mean population doubling of 1. The NRM cell line is capable of forming multinucleate myotubes in confluent cultures and can be stimulated by TGF-B1 to differentiate into chondrocyte-like cells (Seyedin et al., (1985) Proc. Natl. Acad. Sci. USA, Vol. 82, pp. 2267-2271).

The mitogenic responses elicited by the conditioned medium from OSR9TR1 cells were compared to a number of known growth factors. All growth factors were purchased from GIBCO BRL, Life Technologies, Inc., and were tested over a 3-4 log concentration range incorporating the effective concentrations suggested by the supplier. The growth factors were human recombinant platelet derived growth factor-AB heterodimer (PDGF-AB); human recombinant platelet derived growth factor-AA homodimer (PDGF-AA); human recombinant platelet derived growth factor-BB homodimer (PDGF-BB); human recombinant acidic fibroblast growth factor (aFGF); human recombinant basic fibroblast growth factor (bFGF); human recombinant epidermal growth factor (EGF); human recombinant insulin-like growth factor I (IGF-1); human recombinant insulin-like growth factor II (IGF-II); human recombinant transforming growth factor beta, type I (TGF-B1); human recombinant interleukin 1-beta (IL-1B); recombinant murine leukemia inhibitory factor (LIF); recombinant murine tumor necrosis factor alpha (TNF-a). In addition, a mixture of bone morphogenic proteins (BMP-2, BMP-3, BMP-4, and BMP-7) isolated from bovine bone by Koenig et al., (1991) J. Bone Mineral Res., Vol. 6, pp. 206 was included in the analysis. The BMPs have been shown to induce the formation of cartilage and bone in vivo (reviewed by Wozney (1989) Progress in Growth Factor Research, Vol. 1, pp. 267-280) and heparin affinity chromatography was used in the purification of the bone derived BMP mixture.

Fractionation of Mitogenic Growth Factor Produced by OSR9TR1

To gain some information on the types of mitogenic growth factors produced by OSR9TR1 cells, 20 ml of the clarified conditioned medium was applied to a heparin agarose column (1 ml bed volume, type I heparin agarose, purchased from Sigma Chemical Company), and the column was washed with 5.0 ml of 25 mM Tris buffer, pH8.0. After collecting the flow through fraction of the conditioned medium, heparin binding factors were eluted in a stepwise manner by washing the heparin agarose column with 5.0 ml of 0.2M NaCl in 25 MM Tris buffer, pH8.0; followed by 5.0 ml of 1.0M NaCl in 25 mM Tris buffer, pH8.0; and finally 5.0 ml of 2.0M NaCl in 25 MM Tris buffer, pH8.0. All fractions were dialyzed versus water and lyophilized. For analysis of mitogenic activity, the lyophilized fractions were resuspended in 2.0 ml of serum free medium and sterilized by centrifugal filtration (Centrex filters, Schleicher and Schuell).

Figure 1:
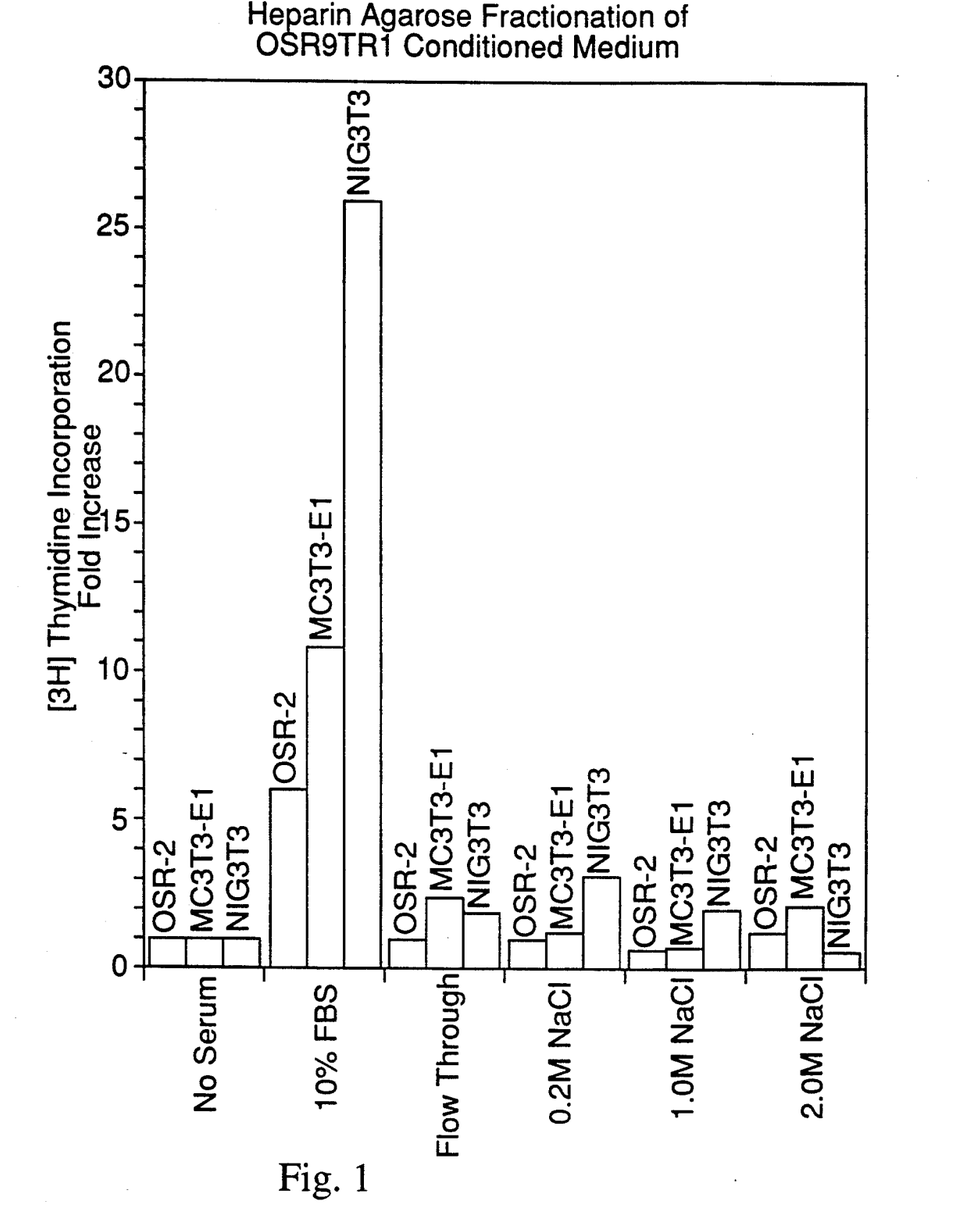
FIG. 1 shows the mitogenic activity of the mitogenic growth factors isolated from OSR9TR1 conditioned medium.
Figure 2A:
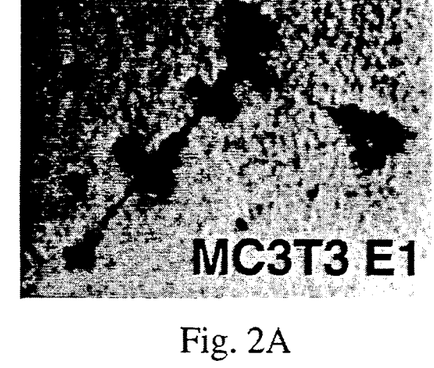
FIGS. 2A, 2B, 2C, 2D, 2E, 2F, 2G, 2H, 2I show the MATRIGEL ™ growth characteristics of the C3H10T½ cell line in the presence of various growth factors and OSR9TR1 conditioned media.
Figure 2B:
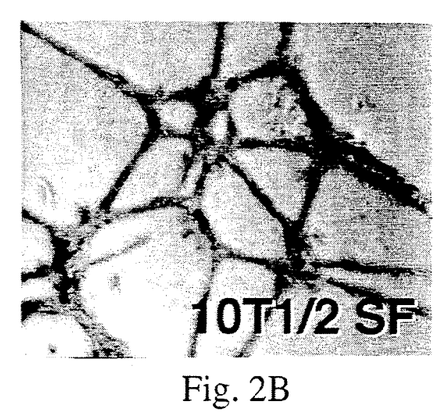
Figure 2C:
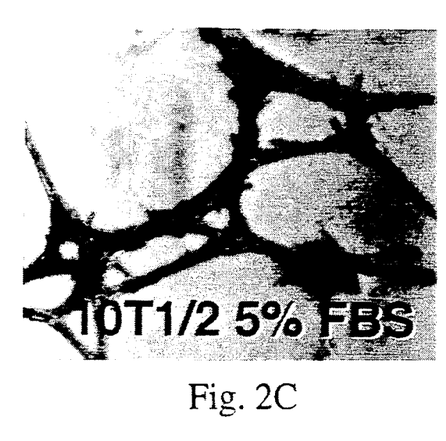
Figure 2D:
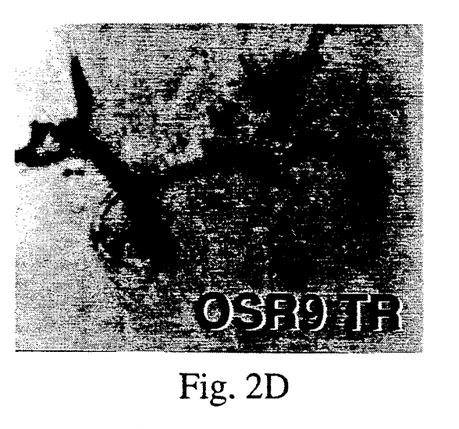
Figure 2E:
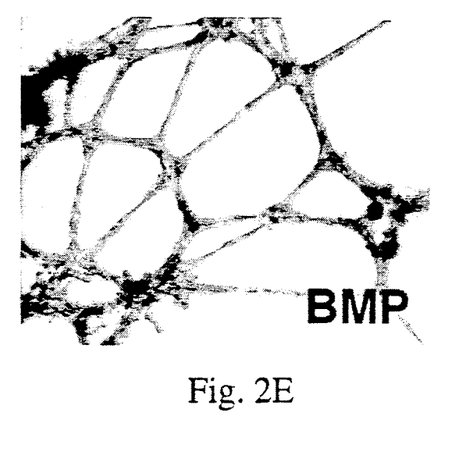
Figure 2F:
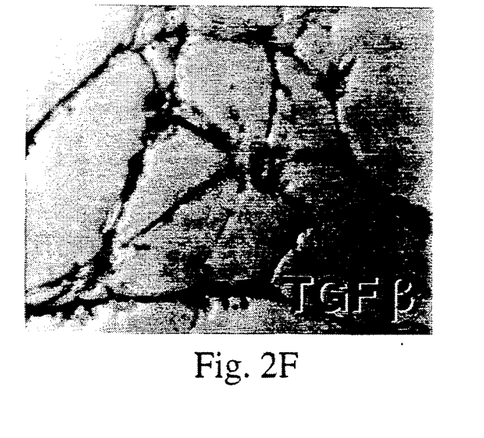
Figure 2G:
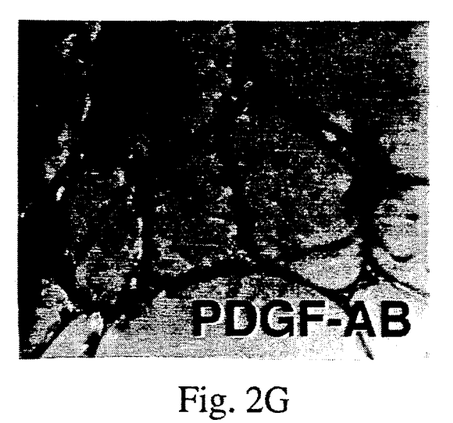
Figure 2H:
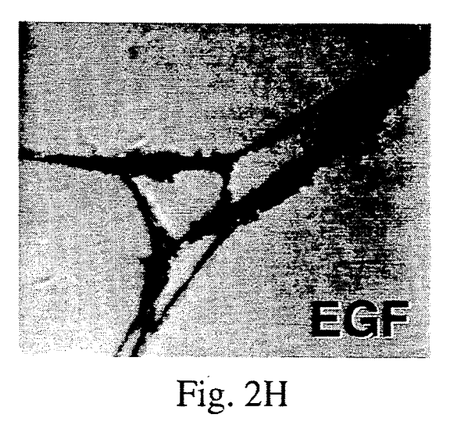
Figure 2I:
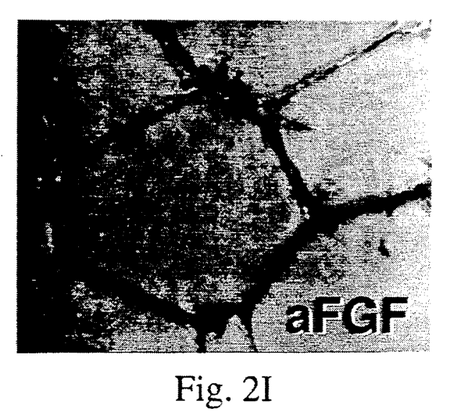

The mitogenic response of cells was quantitated using a [$^3$H]thymidine incorporation assay as previously described (Isfort (1990) Somatic Cell/Molec. Genet. 16:109-121). Briefly, target cells are plated at 2×10$^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. The heparin agarose fractions were added to the serum starved cells in a volume of 50 ul of medium, with serum-free medium serving as a control and 20% FBS (10% FBS final concentration) serving as a positive mitogenic control. After 16 hours incubation, 10 ul of serum-free medium containing 1 uCi of- [$^3$H]thymidine (Amersham, 5 Ci/mmol, 185 MBq/mmol) were added to each well and the cells were incubated for 6 additional hours. The cells were then harvested and lysed on glass fiber filters using a PHD cell harvester (Cambridge Technology, Inc.) and the radioactivity in the samples was assayed by scintillation spectrophotometry. The data were calculated from the mean dpms of quadruplicate samples of the experimental groups and expressed as the fold incorporation relative to the serum-free treated cells. The results are shown in FIG. 1, and Table 2.

TABLE 2

Mitogenesis Results

| Stimulus | Target Cell Line | | | | | |
|---|---|---|---|---|---|---|
| | OSR2 (osteoblast) | MC3TC-E1 (osteoblast) | NRM (multipotent) | C3H10T1/2 (multipotent) | MRC-5 (fibroblast) | NIH3T3 (fibroblast) |
| 0% SERUM | 0 | 0 | 0 | 0 | 0 | 0 |
| 10% SERUM | + | + | + | + | + | + |
| PDGF-AA | + | + | + | + | + | ND |
| PDGF-BB | + | + | + | + | + | ND |
| PDGF-AB | + | + | + | + | + | + |
| EGF | + | + | + | + | + | + |
| aFGF | + | + | + | + | + | + |
| bFGF | 0 | + | 0 | + | 0 | 0 |
| IGF-I | + | + | + | + | + | + |
| IGF-II | + | + | + | + | + | + |
| TGF-B1 | + | (−) | 0 | + | 0 | + |
| IL-1B | + | + | + | + | ND | + |
| LIF | + | 0 | + | 0 | ND | 0 |
| TNF-a | + | + | + | ND | ND | + |
| BMP-2,3,4,7 | + | (−) | 0 | + | + | + |
| OSR9TR1 Conditioned medium | + | + | + | 0 | + | ND |
| HepAg FT | 0 | + | ND | ND | ND | + |
| 0.2M NaCl | 0 | 0 | ND | ND | ND | + |
| 1.0M NaCl | 0 | 0 | ND | ND | ND | + |
| 2.0M NaCl | + | + | ND | ND | ND | 0 |

Table Legend. Comparison of proliferative effects of a variety of mitogens on target cells. 0 = no stimulation (equivalent to 0% serum control). + = mitogenic stimulation at least 50% above the 0% serum control. − = inhibition of proliferation at least 50% of 0% serum control, ND = not determined.

The results of the mitogenicity assay indicate that OSR9TR1 cells produce 4 growth factors that are secreted into the serum-free conditioned medium. The non-heparin binding mitogenic growth factor has an ability to stimulate the proliferation of osteoblastic and fibroblast cell lines. The first heparin binding mitogenic growth factor having a arose elution property of from greater than 0 to less than or equal to 0.2M NaCl, has to stimulate the proliferation of fibroblast cell lines. The second heparin binding mitogenic growth factor having a heparin agarose elution property of from greater than 0.2 to less than or equal to 1.0M NaCl, has an ability to stimulate the proliferation of fibroblast cell lines. The third heparin binding mitogenic growth factor having a heparin agarose elution property of from greater than 1.0 to about 2.0M NaCl, has an ability to stimulate the proliferation of osteoblast cell lines.

Differentiation Growth Factor produced by OSR9TR1 Cells

The C3H10T½ cell line (American Type Culture Collection, CCL 226) has been shown to be capable of expressing multiple new phenotypes when stimulated in an appropriate manner (Taylor and Jones (1979) Cell, Vol. 17, pp. 771–779). In order to determine if the serum-free conditioned medium from OSR9TR1 cells was able to stimulate the osteoblastic differentiation of C3H10T½ cells a MATRIGEL TM growth assay was performed. Osteoblastic cells show a characteristic canalicular cell processes which form a network when cultured on MATRIGEL TM (Vukicevic et al., (1990) Cell, Vol. 63:437–445). Briefly, C3H10T½ cells were plated in 24 well culture dishes at a seeding density of approximately 50,000 cells per well in 1 ml of growth medium and allowed to attach overnight. The next day, the media was removed from the wells, the cells were washed three times with phosphate buffered saline and 1 ml of OSR9TR1 conditioned serum-free medium was applied. The OSR9TR1 conditioned media was prepared as described above for the detection of mitogenic growth factors. In addition, various growth factors were added in 1 ml of serum-free medium. Serum-free medium and growth medium were added to cells and served as experimental controls. The cells were further cultured for 48 hours under standard conditions 37° C. under 5% carbon dioxide/95% air atmosphere. After 48 hours, they cells were transferred to 24 well culture plates containing gelled MATRIGEL TM along with 0.5 ml of the experimentally conditioned medium to which the cells were exposed. In the cases of serum-free media, fetal bovine serum was added in 0.5 ml of fresh medium such that the final concentration was 2.5%. After 3 days of additional culture, the growth pattern on MATRIGEL TM was photographed (FIG. 2).

As can be seen in FIG. 2, the MATRIGEL TM growth characteristics of the C3H10T½ cells in the presence of either C3H10T½ conditioned media alone or C3H10T½ conditioned media and 5% fetal bovine serum resembles a characteristic "endothelial-like" pattern previously described for human umbilical vein endothelial cells (Grant et al., (1989) Cell, Vol. 58, pp. 933–943). In comparison, the OSR9TR1 conditioned media resulted in a change in the MATRIGEL TM growth characteristic of the C3H10T½ cell line from the "endothelial-like" pattern to the "canalicular" pattern which is typical for osteoblastic cells (for example, see the MC3T3-E1 growth pattern in FIG. 2). None of the other growth factors tested, neither the bone morphogenic proteins, TGF-B, PDGF-AB, EGF nor aFGF affected the MATRIGEL TM growth pattern of the C3H10T½ cells (FIG. 2). Accordingly, the OSR9TR1 cell line produces a differentiation growth factor stimulating the differentiation of MC3T3-E1 cells.

FIG. 2 shows that MATRIGEL TM growth characteristics of the C3H10T½ cell line in the presence of various growth factors and OSR9TR1 conditioned media. MATRIGEL TM growth was performed as described in the text. FIG. 2A illustrates MATRIGEL TM growth of MC3T3-E1 cells showing typical canalicular growth of a osteoblastic cell line. FIG. 2B illustrates MATRIGEL ™ growth of C3H10T½ cells in the presence of C3H10T½ cell conditioned media showing typical "endothelial-like" growth pattern. FIG. 2C illustrates MATRIGEL ™ of C3H10T½ cells in the presence of C3H10T½ cell conditioned media and 5% fetal bovine serum. FIG. 2D illustrates MATRIGEL ™ growth of C3H10T½ cells in the presence of OSR9TR1 conditioned media showing canalicular growth pattern. FIG. 2E illustrates MATRIGEL ™ growth characteristics of the C3H10T½ cells in the presence of bone morphogenic proteins. FIG. 2F illustrates MATRIGEL ™ growth characteristics of the C3H10T½ cells in the presence of TGF-B. FIG. 2G illustrates MATRIGEL ™ growth characteristics of the C3H10T½ cells in the presence of PDGF-AB. FIG. 2H illustrates MATRIGEL ™ growth characteristics of the C3H10T½ cells in the presence of EGF. FIG. 2I illustrates MATRIGEL ™ growth characteristics of the C3T10T½ cells in the presence of aFGF.

The invention has been described herein with reference to certain preferred embodiments and examples. Obvious variations may appear to those skilled in the art. Therefore, the invention is not to be considered limited thereto but only by the claims which below.

What is claimed is:

1. A cell line having all the identifying characteristics of American Type Culture Collection Accession No. CRL 11071.

* * * * *

UNITED STATES PATENT AND TRADEMARK OFFICE
CERTIFICATE OF CORRECTION

PATENT NO. : 5,264,358

DATED : November 23, 1993

INVENTOR(S) : C.W. Doersen and R. J. Isfort

It is certified that error appears in the above-indentified patent and that said Letters Patent is hereby corrected as shown below:

Figure 1, "NIG" should read --NIH--.

Column 2, line 12, "amplified a normal" should read --amplified c-myc gene, d) a normal--.

Column 3, line 59, "pl ant" should read --plant--.

Column 5, line 2, "remove" should read --removed--.

Column 6, line 22, "ZVol" should read --Vol--.

Column 6, line 43, "cycle" should read --cycle.--.

Column 6, line 65, "Levi ne" should read --Levine--.

Column 8, line 10, "theses" should read --these--.

Column 8, line 52, "i t" should read --it--.

Column 8, line 65, "MM" should read --mM--.

Column 9, line 4, "MM" should read --mM--.

Column 9, line 57, "SOS" should read --SDS--.

Column 10, line 17, "MM" should read --mM--.

Column 10, line 25, "*Science*p53" should read --*Science* p53--.

Column 10, line 26, "*Science*p53" should read --*Science* p53--.

Column 10, line 27, "*Science*RB" should read --*Science* RB--.

Column 10, line 33 "MM" should read --mM--.

Column 10, line 36, "MM" should read --mM--.

Column 11, line 41, "MM" should read --mM--.

Column 11, line 48, "MM" should read --mM--.

Column 11, line 62, "CM" should read --cm--.

Column 12, line 8, "MM" should read --mM--.

UNITED STATES PATENT AND TRADEMARK OFFICE
CERTIFICATE OF CORRECTION

PATENT NO. : 5,264,358

DATED : November 23, 1993

INVENTOR(S) : C.W. Doersen and R. J. Isfort

It is certified that error appears in the above-indentified patent and that said Letters Patent is hereby corrected as shown below:

Column 12, line 16, "MM" should read --mM--.

Column 14, line 32, "MM" should read --mM--.

Column 14, line 35, "MM" should read --mM--.

Column 15, line 35, "a arose" should read --agarose--.

Column 15, line 36, "has to" should read --has the ability to--.

Signed and Sealed this

Sixth Day of June, 1995

*Attest:*

*Attesting Officer*

BRUCE LEHMAN

*Commissioner of Patents and Trademarks*